United States Patent [19]

Escarguel et al.

[11] Patent Number: 5,091,307
[45] Date of Patent: Feb. 25, 1992

[54] PROCEDURE FOR THE COUNTING, DETECTION AND IDENTIFICATION OF MYCOPLASMS IN GENERAL AND URINOGENITAL MYCOPLASMS IN PARTICULAR AND A BIOLOGICAL MEDIUM SPECIALLY ADAPTED TO THIS EFFECT

[75] Inventors: Claude Escarguel; Marie-Hélène Grosso, both of Sanary sur Mer; Patrick Laconi, Hyeres, all of France

[73] Assignee: Diffusion Bacteriologie du Var-D.B.V., Sanary sur Mer, France

[21] Appl. No.: 363,901

[22] PCT Filed: Sep. 20, 1988

[86] PCT No.: PCT/FR88/00464

§ 371 Date: May 30, 1989

§ 102(e) Date: May 30, 1989

[87] PCT Pub. No.: WO89/02926

PCT Pub. Date: Apr. 6, 1989

[30] Foreign Application Priority Data

Sep. 29, 1987 [FR] France ................... 87 13703
Jan. 7, 1988 [FR] France ................... 88 00176

[51] Int. Cl.$^5$ .......................... C12Q 1/20; C12Q 1/02
[52] U.S. Cl. ........................... 435/34; 435/29; 435/12; 435/10; 435/24; 435/870; 435/14; 435/30
[58] Field of Search ............ 435/296, 32, 34, 299, 435/870, 29, 12, 10, 24, 870, 14, 30

[56] References Cited

U.S. PATENT DOCUMENTS

| 4,208,480 | 6/1980 | D'Amato et al. | 435/34 |
| 4,245,043 | 1/1981 | Lund | 435/33 |
| 4,335,205 | 6/1982 | Greenwood . | |
| 4,598,045 | 7/1986 | Masover et al. | 435/34 |
| 4,721,678 | 1/1988 | Masover et al. | 435/296 |

FOREIGN PATENT DOCUMENTS 0104001 3/1984 European Pat. Off. .
0223685 5/1987 European Pat. Off. .

OTHER PUBLICATIONS

Chemical Abstracts, vol. 74, No. 1, 4 Jan. 1971, p. 116, No. 1480W, Columbus, Ohio, U.S.: M. G. Shepard et al., "Urease Color Test Medium ...".
Chemical Abstracts, vol. 98, 1983, p. 323, abstract No. 68494t, Columbus, Ohio, U.S.
Chemical Abstracts, vol. 72, No. 19, 11 May 1970, p. 93, No. 97624d, Columbus, Ohio, U.S.
Chemical Abstracts, vol. 70, No. 10, 10 Mar. 1969, p. 202, No. 46101g, Columbus, Ohio, U.S.
Biological Abstracts, vol. 72, No. 7, 1981, p. 4980, No. 47908, Philadelphia, Pa., U.S.
Davis (1980) Microbiology,3rd Edition,pp. 785-795-,Harper &Row, Philadelphia.
Difo Manual (1984) Detroit, pp. 638-641, 591-592.

Primary Examiner—Robert A. Wax
Assistant Examiner—David R. Preston
Attorney, Agent, or Firm—Browdy and Neimark

[57] ABSTRACT

This process is essentially characterized by enzymatic reactions which are carried out under anaerobic conditions between a liquid growth medium for mycoplasms containing a dilution medium of the sample of fluid to be analyzed and, on the one hand, a first substrate comprising dehydrated urea or glucose in the presence of a color pH indicator also in dehydrated form and, on the other hand, a second substrate comprising arginine also in dehydrated form or glucose in the presence of a color pH indicator and that the speed of the enzymatic response is followed while noting the time corresponding to the color change of the indicators, the respective quantities of urea and arginine or of glucose, on the one hand, and the concentration and the nutrient composition of the said growth and dilution medium, on the other hand, being first selected and standardized in such a way that for Ureaplasma urealyticum present at a supra or sub-pathological rate, the color change of the indicator is or is not obtained after a given amount of time has lapsed.

10 Claims, 1 Drawing Sheet

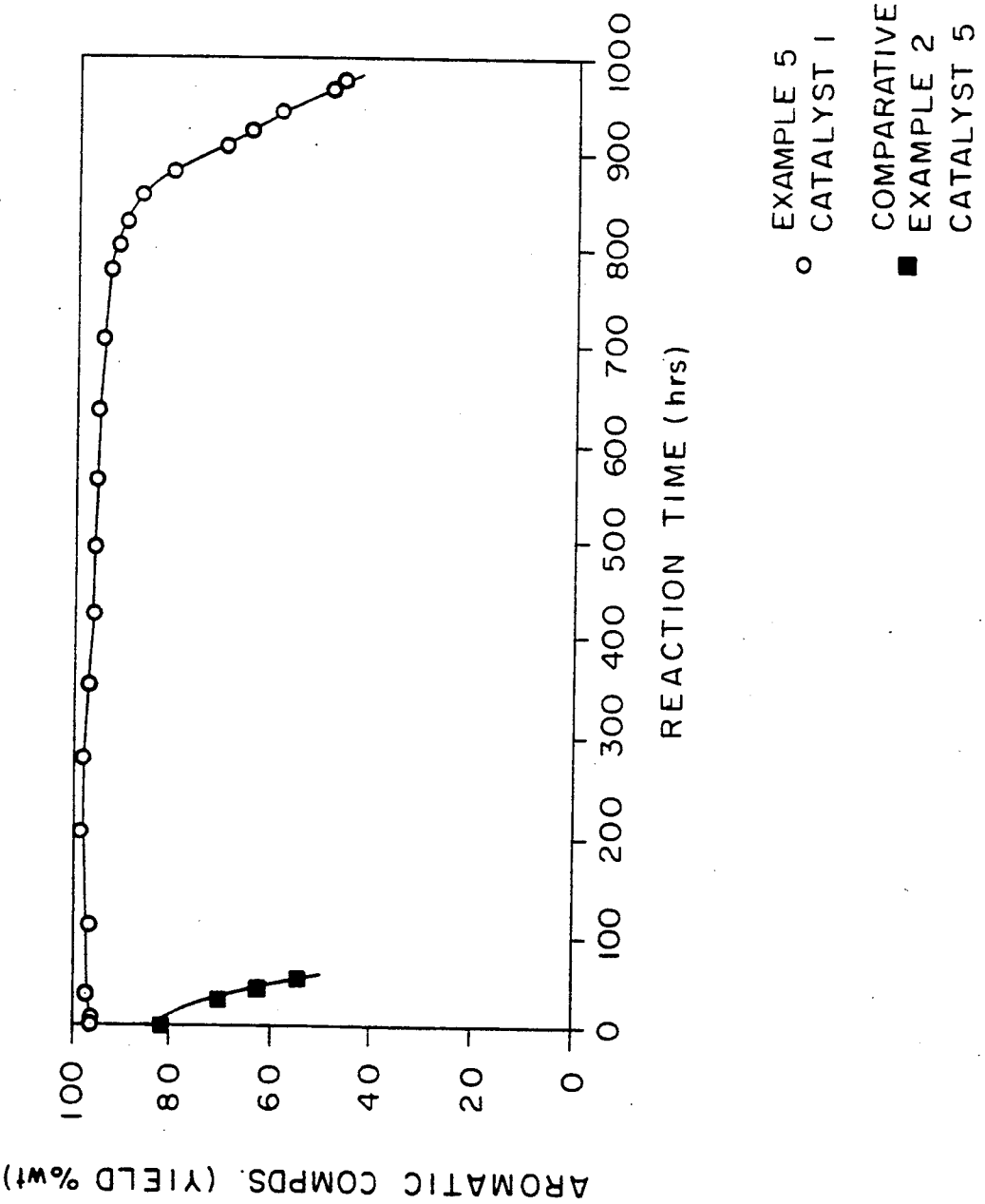

PROCEDURE FOR THE COUNTING, DETECTION AND IDENTIFICATION OF MYCOPLASMS IN GENERAL AND URINOGENITAL MYCOPLASMS IN PARTICULAR AND A BIOLOGICAL MEDIUM SPECIALLY ADAPTED TO THIS EFFECT

FIELD OF THE INVENTION

The present invention relates to a procedure for the counting, detection and identification of mycoplasms in general and urinogenital mycoplasms in particular. An object of the invention is also a biological medium specially adapted to this effect.

BACKGROUND OF THE INVENTION

It is known that mycoplasms are bacteria without walls endowed with enzymatic properties (urease for *Ureaplasma urealyticum* and arginine decarboxylase for *Mycoplasma hominis* and *fermantans*).

These enzymatic properties are used for the identification and counting of the strains in the urinogenital samples.

In effect, these micro-organisms are commensal bacteria (present on perfectly healthy individuals' mucous membrane at a rate slightly lower or equal to $10^3$ CCU/ml—unit of colour change/ml—). When an infection breaks out or when a mucous membrane is rendered fragile (viral infection, bacteria, hormonal imbalance, etc.), they can proliferate and lead to states of chronic superinfection which can result:

either in tubular sterility;
or in masculine sterility;
or in acute or chronic salpingitis;
or in uretroprostatis syndrome;
or in endocervical dysplasia (when they superinfect viral infections: Papilloma virus, herpes, CMV, etc.).

In all the cases in question, they are present at a suprapathological rate higher or equal to $10^4$ CCU/ml.

Until now two techniques were used for the counting of urinogenital mycoplasms:

1. The number of colonies per microscopic field were counted on an isolating gelose.

This technique can be compared to that used for the counting of bacteria in urinary infections (Kass).

However, this type of counting has the inconvenience of systematically using a solid gelose, which is expensive, and is not well adapted for the systematic research of urinogenital mycoplasms. Furthermore, the technique necessitates an incubation in an anaerobic jar.

2. A counting based on the dilution in a series of the sample to be analysed in a liquid medium ($U_9$ for *U. urealyticum*, $M_{42}$ for *M. hominis*) and on the end-point of the appropriate colour indicator of the phenol red type contained in the dilution medium.

However, this technique using the enzymatic properties of urinogenital mycoplasms has several inconveniences:

the urea, in complex liquid medium, is unstable. Because of this its concentration (representing the enzymatic substrate) can vary from one series of tests to another, inducing the risk of a lack of reproducibility;

a reading is not possible until after the colour changes of the indicator have stabilised for at least 24 hours, which involves a minimum response waiting period of 72 hours;

the technique of dilutions in a series is cumbersome and furthermore is marred by a margin of error due to the manipulation;

no commercial kit exists containing all of the necessary reagents as well as other materials.

SUMMARY OF THE INVENTION

The present invention proposes to avoid these inconveniences and provides a process for the counting and detection of mycoplasms using enzymatic kinetics.

Although this last technique, in effect, is known to be used in biochemistry to assay enzyme activity, its use has never been suggested or envisaged to be used for the assay of bacteria, as is the case in the process of the present invention.

The Applicant has found, in effect, that the speed of the enzymatic response was proportional to the quantity of mycoplasms present in the sample to be analysed.

This process is essentially characterized by the fact that the enzymatic reactions are carried out under anaerobic conditions between a liquid growth medium for mycoplasms serving as a dilution medium of the sample of fluid to be analysed, a first substrate comprising dehydrated urea in the presence of a pH colour indicator also in dehydrated form and a second substrate comprising arginine in dehydrated form in the presence of a pH colour indicator. The speed of the enzymatic response is followed by noting the corresponding time for the colour-change of the indicators, the respective quantities of urea and arginine, on the one hand, and the concentration and the nutritious components of the growth and dilution media, on the other hand, being first selected and standardised in such a way that for the *Ureaplasma urealyticum*, present at a supra- or subpathological rate, the turning-point of the colour indicator is or is not obtained after a certain amount of time has lapsed.

According to other features:

the pH indicator is selected with a colour change between pH 6.4 and pH 8;

the pH indicator of choice is phenol red;

the concentration of dehydrated urea and of pH indicator, the concentration of the growth and dilution liquid medium and the quantity of the fluid to be analysed in this medium, are selected in such a way that at a supra-pathological rate (higher or equal to $10^4$ CCU/ml) of *Ureaplasma urealyticum*, the indicator turning-point occurs after a time lapse of 24 hours. At a sub-pathological rate of *U. urealyticum* (lower or equal to $10^3$ CCU/ml), the indicator change occurs after a time lapse of 48 hours;

the concentration of dehydrated arginine and of the pH indicator, the concentration of the growth and dilution liquid medium, and the quantity of fluid to be analysed in this medium, are selected in such a way that the indicator turning-point occurs in 24 or 48 hours for the suprapathological rate (higher or equal to $10^3$ CCU/ml) of *M. hominis* and *fermantans* with no turning-point in 48 hours for the sub-pathological rate (lower or equal to $10^3$ CCU/ml);

the dilution medium of the sample to be analysed is essentially based on a growth broth for mycoplasms added with the appropriate nutritious elements;

the dilution medium for the sample to be analysed advantageously comprises a mycoplasm broth, colt serum, ampicillin, an antibiotic, a reducing agent of the sodium thioglycolate type, yeast and cysteine.

The process according to the invention is preferably carried out in small-sized wells, some of which contain dehydrated urea and some of which contain dehydrated arginine and, after the liquid for analysis has been introduced into them, anaerobic conditions are produced by covering each well with an inert oily substance such as paraffin oil.

The selection of the concentrations and the standardisation of the reagents for putting the process of the invention into operation are made by drawing up a calibration curve starting from the countings according to the two usual techniques mentioned above.

More particularly, the object of the invention is also a unique medium which allows the process in question to be put into operation, in a simple manner, requiring only a limited number of manipulations, while corresponding to three criteria:

to be stable and able to be stored in a laboratory as well as transported;

to allow the mycoplasms to keep their viability while waiting to be put in their growth medium;

not to influence the quantitative counting of the results.

To reconcile these three necessities, a lyophilisate regeneration medium is intended to be used in the present invention as a transport medium for the sample to be analysed. In effect, mycoplasms are bacteria without walls; they are very sensitive to variations in osmotic pressure and have to be introduced quickly into a growth or conservation medium. The disadvantage of growth media is their poor stability, which requires very strict stock management by the users in the sample centres. It should be recalled that the inconvenience of transport media is the dilution effect when the sample is introduced into them before it is put in the growth medium; this totally alters the quantitative counting which is required for calculation of the result.

By unique medium, in the present application, a reactive medium actually in the lyophilised form is understood. This medium is already regenerated or is to be regenerated with a dilution medium. Said reactive medium stabilised in the presence of its diluent is equally understood.

Thus, the unique medium according to the invention comprises a first so-called reactive phase made up of:
known elements necessary for mycoplasm culture of the cholesterol type, yeast extracts, colt serum,
visualization elements of the mycoplasm metabolism of the urea, arginine or glucose type,
a colour indicator (preferably phenol red) and
at least one antibiotic;
and a second phase, comprising a dilution medium also serving as a vehicle for the sample to be analysed, this medium essentially comprising a known specific broth of mycoplasms with 1 g/1000 of agar-agar added and optionally containing an antibiotic.

According to other features:
the antibiotic or antibiotics present in the first phase is (or are) also in the second dilution phase;
this antibiotic(s) is selected from antibiotics of the ampicillin, trimethoprim and nystatin type and preferably from antibiotics acting on the synthesis of folic acid; these are totally ineffective on mycoplasms;
the dilution medium is free from all unstable elements, so making it suitable as a transport and conservation medium of a sample given to be analysed at +4° C.

DETAILED DESCRIPTION OF THE INVENTION

Other features and advantages of the invention emerge more clearly in the following description and example:

According to the general operational mode of the process of the invention, at least two wells of a type known per se having a diameter of 9 mm and a depth of 6 mm are used.

In one of these wells, a quantity of 1 mg (milligram) of dehydrated urea was introduced and in the other a quantity of 1.68 mg (milligram) of dehydrated arginine was introduced. In each of these wells, 6.8 $\mu$g (microgram) of the same dehydrated pH indicator, known as phenol red, was also introduced.

The sample taken from a sick person for analysis purposes was dissolved using the medium indicated below (medium A3) corresponding to the following composition and obtained starting from a dehydrated mycoplasm broth (25.5 g) dissolved in 713 ml of distilled water. The resulting liquid medium had the following added:

200 ml of colt serum;
0.5 g of ampicillin;
8 g of Bactrim ® (antibiotic) from Hoffman Laroche, comprising sufamoxole and trimethoprim;
0.5 g of reducing agent (sodium thioglycolate);
100 ml of yeast extract;
2.5 ml of cysteine (4%).

Each of the wells was covered by a few drops of paraffin oil to create the anaerobic conditions necessary for the enzymatic reactions.

This composition and the quantities of urea, arginine and pH indicator were adapted by carrying out comparative tests using the two traditional techniques currently used, in such a way as to obtain the colour change in 24 hours for the supra-pathological rate for *U. urealyticum* and the colour change in 24 or 48 hours for the suprapathological rate for *M. hominis*.

For these comparative tests, in the said technique of dilution, the traditional liquid dilution medium based on urea and arginine was used, at a rate of 150 $\mu$l of medium, into which 15 $\mu$l of the medium A3 cultured with the sample taken was introduced, with dilution in series at a rate of 15 $\mu$l for each test taken.

For the counting technique per plate (gelose A7), one proceeded as usual, in the evaluation of the mean numbers of colonies of mycoplasms in the microscope field (at a magnification of 100), in the following manner, CFU/ml signifying "colony forming unit"

| less than 1 colony: | concentration of bacteria $\leq 10^3$ CFU/ml |
| from 1 to 5 colonies: | close to $10^4$ CFU/ml |
| from 6 to 10 colonies: | close to $10^5$ CFU/ml |
| from 11 to 20 colonies: | close to $10^6$ CFU/ml |
| over 20 colonies: | $> 10^6$ CFU/ml |

By proceeding in this way starting with urinogenital samples taken from male or female patients, the correspondence between the different techniques was established. This is shown in the following table.

| PATIENT ARG WELL | COUNTING IN LIQUID MEDIUM | MEDIUM A7 | | UREA WELL |
|---|---|---|---|---|
| | | No of colonies | counting | |
| A | $10^6$ in 96 h | >20 | $10^6$ | Positive 24 h |
| B | $10^3$ in 72 h | <1 | $\leq 10^3$ | Positive 48 h |
| C | 0 in 96 hours | 0 | 0 | — |
| D | $10^6$ in 72 h | 12 | $10^6$ | Positive 24 h |
| E | 0 in 96 h | 0 | 0 | — |
| F | $10^1$ in 72 h | 0 | 0 | — |
| G | contamination | 10 U | $10^5$ | Positive 24 h |
| | Positive 24 h (unclear) | >20 M | $10^6$ | (unclear) |
| H | $10^4$ in 72 h | 3 | $10^4$ | Positive 24 h |
| I | $10^5$ in 48 h | 7 | $10^5$ | Positive 24 h |

Reference is also made to the curve shown in the appendix.

On examining this table and the attached comparative curve, it can be noted that for *U. urealyticum* present at a higher or equal rate to $10^4$ CCU/ml, the well with urea changes colour (indicator turning-point) in 24 hours. The colour change of this same well in 48 hours corresponds either to the presence of *U. urealyticum* at a lower or equal rate to $10^3$ CCU/ml (without significance in human pathology), or to chemical or bacterial interference. The urea wells have a great sensitivity: no colour change in 48 hours in the urea well confirms the total absence of *U. urealyticum* even at a low rate ($10^2$ to $10^3$ CCU/ml) the great sensitivity of the urea wells being given.

Furthermore, it can be noted that no interference (bacterial or chemical) can alter the response in 24 hours, resulting in a perfect reliability of detection which can always be verified by transferring the A3 medium on a solid gelose A7 (while using the wells for a screening).

For *M. hominis* and *fermantans*, the enzymatic activity being weaker, only a colour change in the arginine well (ARG) in 48 hours allows the detection of a sub-pathological rate (lower or equal to $10^3$ CCU/ml with no colour change in the well in 48 hours) and supra-pathological rate (higher or equal to $10^4$ CCU/ml with a colour change in the well in 24 or 48 hours).

It follows that the colour change of the urea well in 24 hours and in the arginine well in 24 hours or 48 hours are interesting. The micro-biologist can therefore, in this time lapse, confirm whether or not there is an infection or superinfection of a mucous membrane by a mycoplasm.

In reference to the above table, it is noted that for patient F, the results correspond to a concentration which does not seem to be detected by the present technique. This is due to the fact that the threshold of sensitivity of the wells was voluntarily fixed at $10^3$ CCU/ml. The lower concentrations do not have any interest in the diagnosis of mycoplasm infections. It is normal not to find colonies on the medium A7, because the technique of direct inoculation induces a dilution factor.

As for patient G, it is noted that only the counting per plate can be interpreted.

It is noted that the countings carried out by means of the three techniques in question lie in a straight correspondence line between the gelose A7 technique and the dilution technique and are situated on the changing kinetic curve corresponding to it (24 hours for the higher or equal concentrations at $10^4$ CCU/ml and 48 hours for the lower concentrations at $10^3$ CCU/ml).

As indicated previously, it is noted on the attached graph, that only patient F does not lie on this straight line.

It is noted that for the supra-pathological concentration, the time limit for obtaining values by the dilution technique is 72 hours, 48 hours for the counting plates, 24 hours with the counting in wells, according to the present invention.

Moreover, the Applicant notes that the new technique according to the invention and using enzyme kinetics on the supports containing the dehydrated substrate, has a very good correlation in 95% of the cases when compared to the two other techniques used.

The 5% margin of error, noted in the course of several experiments can be attributed:

either to strains which preferentially grow in liquid media, as is the case when the counting on solid gelose is wrongly used;

or with strains which have a weak enzymatic activity, as is the case where the only countings on plates gives low values.

Therefore, it can be observed that the detection of this 5% margin of error can be made by simultaneously using the two methods of counting, one of the present invention and one with solid gelose.

Furthermore, enzyme kinetics in wells according to the present invention, in which the substrate exists in the dehydrated form, has, with respect to the dilution technique in series, the following advantages:

stability of the substrate guaranteeing reproductibility;

fewer manipulations and elimination of imprecision resulting from manual dilutions on micro-plates with the small samples used in the assay;

response waiting time of 24 rather than 72 hours;

and finally a cost price reduction when all the materials used are taken into account.

A particular operational mode uses the unique medium described previously in the present invention.

The sample to be analysed from a patient (a urinogenital sample was taken here as the example) is introduced as an aliquot of the so-called dilution medium and stored in a flask.

If the active phase exists in lyophilised form, the so-called reactive medium is "regenerated" by the addition of dilution medium. Clearly, if the reactive medium is already diluted and stabilised itself, it is used as it is.

An aliquot of the medium containing the sample is poured into an aliquot amount of the reactive medium. The detection, that is, visualisation of the presence of the bacteria under test, is made evident by the colour change of the indicator turning-point (from yellow to red). Furthermore, the medium remains clear because urinogenital mycoplasms, in contrast to other bacteria, do not cloud the medium.

The counting of mycoplasms whose presence is made evident, is carried out by the enzyme kinetic procedure described above. This technique is used to advantage in active media (regenerated), as described in the invention, to establish a differential diagnosis between the strains present at a supra-pathological rate (higher or equal to $10^3$ CCU/ml: colour change in 24 hours) and those present at a sub-pathological rate (lower or equal to $10^2$ CCU/ml; colour change in 48 hours or more).

In cases where the counting is of less practical interest (search for mycoplasms at a very low rate, e.g. in the case of the supervision of in vitro fertilisation, examination of sperm, in haemocultures or in surgical removal in salpingitis), the observation of the end-point in the medium is made after the first 24 hours.

In all other cases in question, the technique used for the counting, in particular the technique of enzyme kinetics, directs the practitioner towards the level of mycoplasms present in the sample taken.

For the identification of the mycoplasms it is intended, according to the invention put forward here, to follow up the operations of detection and counting carried out with the biological medium, by identification of the mycoplasms using their sensitivity profile to antibiotics (antibiogram).

In effect, such an antibiogram of the mycoplasms not only establishes that the colour change of the unique medium shown here is definitely due to a mycoplasm, and not to other bacteria having identical enzymatic activity, but also the profile found allows the confirmation of which type, species and genus is present. As soon as the change of colour of the indicator is noted and the medium is still clear (24 hours for example for the traditional urinogenital samples taken, urethra, vagina, endocol, and above 24 hours for the other cases cited above), the operation of this phase of identification is carried out on the same multiplate well, regrouping the identification characteristics and the antibiotics to be tested with a second aliquot of another reactive medium identical to the first, to which the previous medium used is added.

Thus, it can be observed and noted that the profile of this type of multiplate well is well known in the technique, which allows differentiation between *Ureaplasma* and *Mycoplasma* (*hominis* or *fermantans*) and the assessment of the sensitivity of the isolated strain to the antibiotics present (results from 24 to 48 hours).

It can also be seen that with this unique medium, supplemented with a specific antibiogram multiplate well, it is possible to achieve, in from 48 to 72 hours, the transport of a sample, the detection, quantitative evaluation, identification and sensitivity to antibiotics, more particularly 98% of urinogenital mycoplasm strains responsible for infections (*Mycoplasma fermantans* represents less than 2% of this pathology; it is however detected, although assimilated with hominis by its arginine-positive character).

The interest of the medium in this invention therefore lies in:

1. The simplicity of the technique.
2. The absence of false positives (Contaminants seldom show their enzymatic characteristics in 24 hours. Furthermore, the semi-gelose medium allows the presence of possible contaminants resistant to ampicillin, trimethroprim and nystatin; such contaminants cloud the medium.

However, if certain strains sensitive to the antibiotic mixture present in the medium of the invention (liquid remaining clear) express their enzymatic urea or arginine-positive character (broth clear red), it would be impossible to falsely render a test positive, it being given that the antibiogram multiplate well would show an aberrant profile and the possible colour change of the well containing "contaminant" present in this multiplate well.

3. The possibility of having a stable transport medium (separation of the labile factors present in the lyophilisate).
4. The possibility of systematically introducing in the diagnosis of the mycoplasms a sensitivity study to the antibiotics. This is all the more justified in that 15% of the strains are resistant to tetracyclines and more than 30% of *Ureaplasma urealyticum* and 97% of *Mycoplasma hominis* are resistant to erythromycin (Congress I.C.A.A.C. 25 New York, 1987).

5. The possibility of diagnosing in a precise manner 10% of the strains growing preferentially in a liquid medium, which until now were impossible to distinguish from possible contaminants (urea or arginine-positive and sensitive to the antibiotics present in the medium: clear media having changed to red. Example: campylobacter, certain anaerobic or microaerophilic bacteria of the vaginal flora). As these 10% of strains do not grow on solid isolating geloses, the diagnosis was always uncertain.

6. The possibility of totally eliminating the anaerobic conditions in anaerobic jars or sachets, which are relatively expensive and sometimes too sophisticated for non-specialised laboratories.

It goes without saying that the present invention has only been described only in a purely explanatory manner and is no way limiting. All possible useful modifications can be brought about as equivalents without exceeding the scope of the present invention.

It is particularly in this way that the unique medium according to the invention can also be used for diagnosing pneumonary mycoplasms (an example of which are atypical pneumopathies) by means of using glucose instead of urea and arginine, together with the appropriate indicator (Thymol Blue).

We claim:

1. A method for the detection and quantitation of mycoplasmas comprising:
    reacting a sample to be analyzed under anaerobic conditions in a liquid mycoplasma growth medium to obtain an enzymatic response, said mycoplasma growth medium also being used as dilution medium for the sample to be analyzed, said sample reacted with:
    (a) a first substrate consisting essentially of dehydrated urea in the presence of a dehydrated colored pH indicator;
    (b) a second substrate consisting essentially of dehydrated arginine in the presence of a colored pH indicator; and
    (c) an optional third substrate comprising glucose in the presence of a dehydrated pH indicator; and
    measuring the enzymatic response by measuring the time required for the pH indicators to change color;
    the respective amounts of urea and arginine and the concentration and the composition of the growth medium having been chosen and standardized such that, for *U. urealyticum* and *M. hominis* or *M. fermentans* or pulmonary mycoplasmas present at supra- or sub-pathological levels, any color change of the pH indicators is obtained within a predetermined length of time; wherein supra-pathological levels of mycoplasmas are levels greater than $10^4$ CCU/ml, and sub-pathological levels of mycoplasmas are levels less than $10^3$ CCU/ml.

2. The method according to claim 1 wherein the pH indicator changes color at a pH between 6.4 and 8.

3. The method according to claim 2 wherein the pH indicator is selected from the group consisting of Phenol Red and Thymol Blue.

4. The method according to claim 1 wherein the concentration of dehydrated urea and the pH indicator in said first substrate and the concentration of growth medium and the quantity of fluid sample to be analyzed are such that, at suprapathological levels of *U. urealytium*, the color change of the pH indicator occurs within 24 hours and that at subpathological levels of *U. urealyticum* the color change of the pH indicator occurs within 48 hours.

5. The method according to claim 1 wherein the concentration f dehydrated arginine and the concentration of the pH indicator in said second substrate and the concentration of growth medium and the quantity of sample to be analyzed are such that, at suprapathological levels of *M. hominis* and *M. fermentans*, the color change of the pH indicator occurs within from 24 to 48 hours and that for subpathological levels of *M. hominis* and *M. fermentans*, no color change occurs within 48 hours.

6. The method according to claim 1 wherein the dilution medium for the sample to be analyzed is based upon a mycoplasma growth broth supplemented with appropriate nutritional elements.

7. The method according to claim 6 wherein the dilution medium for the sample to be analyzed comprises mycoplasma broth, foal serum, ampicillin, an antibiotic, a reducing agent of the sodium thioglycolate type, yeast extract and cysteine.

8. The method according to claim 1 wherein the method is conducted in wells of small dimensions, a first set of wells containing a substance selected from the group consisting of urea and glucose, and a second set of wells containing a substance selected from the group consisting of dehydrated arginine and glucose, and said wells are covered with an inert oil to establish anaerobic conditions.

9. The method according to claim 8 wherein said inert oil is paraffin oil.

10. The method according to claim 1 wherein the concentrations and the reagents are obtained by establishing a correlation curve using numerations according to conventional techniques.

* * * * *